United States Patent
Higuchi

(10) Patent No.: US 10,474,869 B2
(45) Date of Patent: *Nov. 12, 2019

(54) AUTHENTICATION APPARATUS AND PRISM MEMBER FOR AUTHENTICATION

(71) Applicant: NEC Corporation, Minato-ku, Tokyo (JP)

(72) Inventor: Teruyuki Higuchi, Tokyo (JP)

(73) Assignee: NEC CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/125,879

(22) Filed: Sep. 10, 2018

(65) Prior Publication Data

US 2019/0080143 A1    Mar. 14, 2019

Related U.S. Application Data

(63) Continuation of application No. 15/107,192, filed as application No. PCT/JP2014/083673 on Dec. 19, 2014.

(30) Foreign Application Priority Data

Dec. 27, 2013   (JP) ................................ 2013-272614

(51) Int. Cl.
  *G06K 9/00*    (2006.01)
  *A61B 5/1172*  (2016.01)
  *A61B 5/00*    (2006.01)

(52) U.S. Cl.
  CPC ........ *G06K 9/00087* (2013.01); *A61B 5/0077* (2013.01); *A61B 5/1172* (2013.01);
  (Continued)

(58) Field of Classification Search
  CPC ........... G06K 9/00046; G06K 9/00087; G06K 9/00107; A61B 5/1172
  See application file for complete search history.

(56) References Cited

U.S. PATENT DOCUMENTS 6,127,674 A   10/2000  Shinzaki et al.
6,292,576 B1   9/2001  Brownlee
(Continued)

FOREIGN PATENT DOCUMENTS

CN    101201896 A    6/2008
CN    201233606 Y    5/2009
(Continued)

OTHER PUBLICATIONS

International Search Report for PCT Application No. PCT/JP2014/083673, dated Mar. 3, 2015.
(Continued)

*Primary Examiner* — Kenny A Cese

(57) ABSTRACT

An authentication apparatus comprises a prism member, an imaging unit, and a visible light source configured to radiate visible light to a living body. The prism member has a substantially trapezoidal shape with at least one side face thereof formed in an expanded shape from a living body authentication face against which an authentication portion of the living body is put, toward an imaging face that is parallel to the living body authentication face. The visible light source is disposed below the imaging face and near a side of an expanded side of the imaging face. The imaging unit is disposed below the imaging face.

6 Claims, 15 Drawing Sheets

(52) U.S. Cl.
CPC ..... G06K 9/00046 (2013.01); G06K 9/00107 (2013.01); *A61B 2562/0233* (2013.01)

(56) References Cited

U.S. PATENT DOCUMENTS

| | | | |
|---|---|---|---|
| 6,381,347 B1 | 4/2002 | Teng et al. | |
| 6,414,749 B1* | 7/2002 | Okamoto | G06K 9/00046 356/71 |
| 2008/0112600 A1 | 5/2008 | Miura | A61B 5/02007 382/125 |
| 2008/0310690 A1 | 12/2008 | Higuchi | G06K 9/00046 382/124 |
| 2009/0214083 A1 | 8/2009 | Sato | A61B 5/117 382/107 |
| 2011/0163163 A1* | 7/2011 | Rowe | G06K 9/00046 235/462.25 |
| 2012/0306815 A1 | 12/2012 | Su | G06F 3/042 345/175 |
| 2014/0023249 A1 | 1/2014 | Higuchi | |
| 2014/0153791 A1 | 6/2014 | Kim | G06K 9/00046 382/124 |
| 2015/0062319 A1 | 3/2015 | Higuchi | |

FOREIGN PATENT DOCUMENTS

| | | |
|---|---|---|
| CN | 201255886 Y | 6/2009 |
| CN | 103443822 A | 12/2013 |
| JP | H11-83459 A | 3/1999 |
| JP | 2000-194829 A | 7/2000 |
| JP | 2001-142606 A | 5/2001 |
| JP | 2001-283207 | 10/2001 |
| TW | 200825942 A | 6/2008 |
| TW | 201250553 A | 12/2012 |
| WO | 2013/146761 A1 | 10/2013 |

OTHER PUBLICATIONS

Taiwan, Search Report for Taiwan Application No. 103145153 dated Dec. 21, 2016.
Japanese Office Action for JP Application No. 2016-076306 dated Sep. 28, 2016 with English Translation.

* cited by examiner

AUTHENTICATION APPARATUS AND PRISM MEMBER FOR AUTHENTICATION

The present application is a continuation application of U.S. patent application Ser. No. 15/107,192 filed on Jun. 22, 2016, which is a National Stage Entry of international application PCT/JP2014/083673 filed Dec. 19, 2014, which claims the benefit of priority from Japanese Patent Application 2013-272614 filed on Dec. 27, 2013, the disclosures of all of which are incorporated in their entirety by reference herein.

TECHNICAL FIELD

The present invention relates to an authentication apparatus and a prism member for authentication.

BACKGROUND ART

Commonly used living body authentication apparatuses using fingerprints, which are a kind of living body feature, to authenticate individuals employ a method using a critical angle of total reflection by a triangular prism (for example, see Patent Literature 1). The method involves reading bumpiness (ridges and furrows) of a skin surface, which enables a fingerprint image to be easily obtained with high contrast. The method has thus highly compatible with "fingerprinting" wherein fingerprints are collected by impressing an inked fingertip against paper, and the method has been used in judicial and police purposes.

CITATION LIST

Patent Literature

Patent Literature 1: U.S. Pat. No. 6,381,347

SUMMARY OF INVENTION

Technical Problem

Meanwhile, in a related living body authentication apparatus using a prism method, light sources for capturing fingerprints are disposed below a prism, as shown in FIG. 15.

When the light sources are disposed below the prism, there is a problem that a light amount can be secured but a living body authentication face of the prism against which a finger is put turns into a mirror face, so that the light sources are reflected on the mirror face and appear in an image at the time of capturing fingerprints, and the fingerprints etc. suitable for authentication cannot be captured as an authentication image.

As one method for solving the above-described problem, a method is used for disposing a light source on the side face side. When this disposition method is used, the light source is not reflected on a prism face against which a finger is put, and reflection of the light source does not occur at the time of capturing fingerprints. However, there is a problem that a light amount for capturing an authentication image suitable for authentication cannot be secured. Moreover, there is a problem that since the light source is disposed on the side face side of the prism, a length in the lateral direction of an authentication apparatus becomes large, and as a result, it is difficult to avoid the size of the authentication apparatus becoming larger.

In order to solve the above-described problems, it is an object of the present invention to provide an authentication apparatus and a prism member.

Solution to Problem

The present invention is an authentication apparatus comprising a prism member, an imaging unit, and a visible light source configured to radiate visible light to a living body, wherein said prism member has a substantially trapezoidal shape with at least one side face thereof formed in an expanded shape from a living body authentication face against which an authentication portion of said living body is put, toward an imaging face that is parallel to said living body authentication face, said visible light source is disposed below said imaging face and near a side of an expanded side of said imaging face, and said imaging unit is disposed below said imaging face.

The present invention is a prism member for authentication of a living body, comprising a living body authentication face configured to put an authentication portion of said living body;

and an imaging face configured to be parallel to said living body authentication face, wherein said prism member has a substantially trapezoidal shape with at least one side face thereof formed in an expanded shape from said living body authentication face toward said imaging face.

Advantageous Effects of Invention

According to the present invention, an image with little influence of a light source can be captured.

DESCRIPTION OF EMBODIMENTS

The following describes embodiments of the present invention in detail.

First, the principle of a prism according to the present invention will be described. While the following description addresses a case in which a living body is a finger, the present invention is not limited thereto. For example, it may be applied also to palmprint authentication of a palm.

Figure 1:
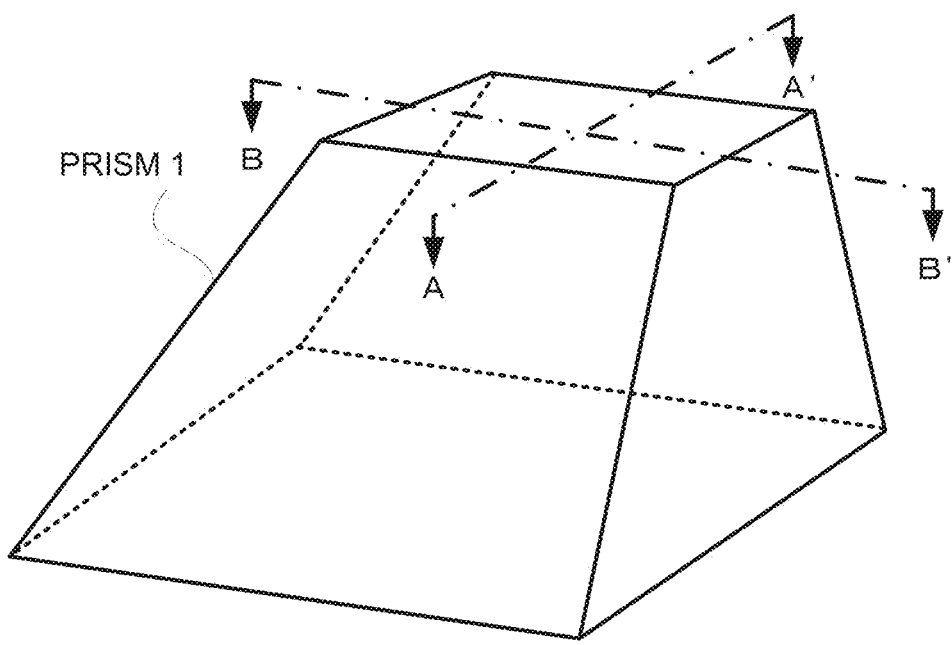
FIG. 1 is a diagram showing a configuration of a prism 1 according to the present invention.
Figure 2:
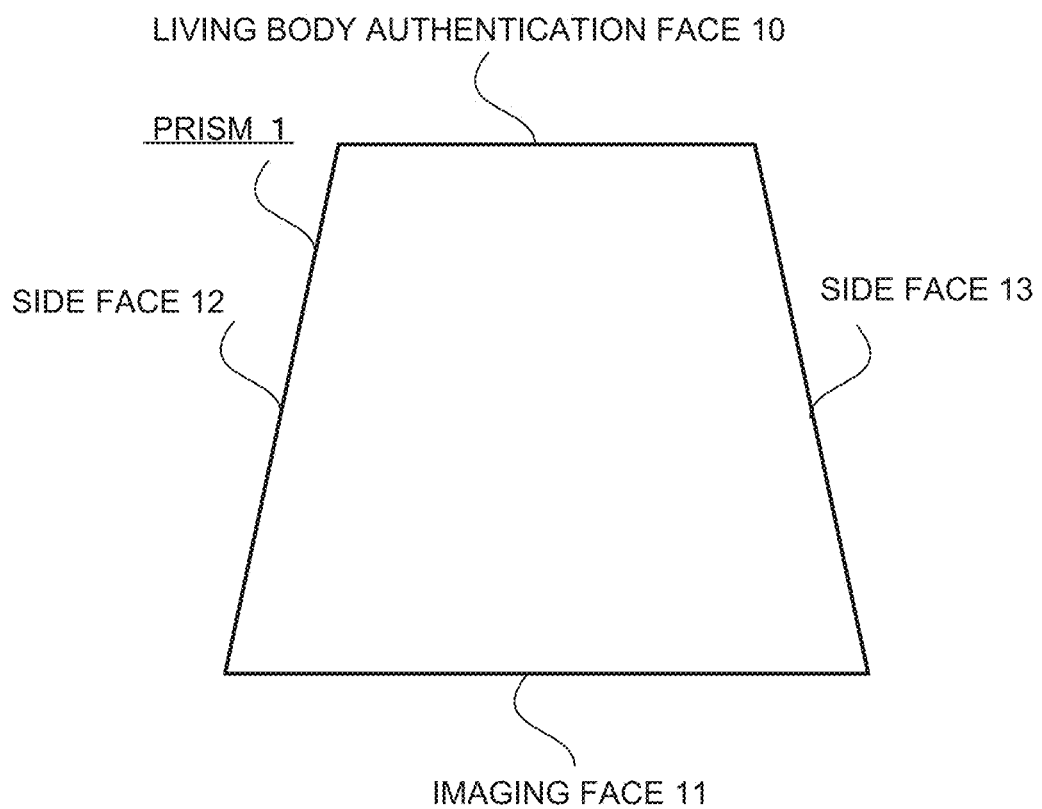
FIG. 2 is a cross-sectional diagram along an A-A' line of the prism 1.

FIG. 1 is a perspective diagram of a prism 1 as one example of the prism according to the present invention, and FIG. 2 is a cross-sectional diagram along an A-A' line of the prism 1.

Further, in figures, reference numeral 10 designates a living body authentication face against which a living body (for example, a finger) is put, 11 designates an imaging face that is formed generally parallel to the living body authentication face 10 and is a face on the side on which an imaging device such as a camera is disposed, and 12 and 13 designate side faces.

Figure 3:
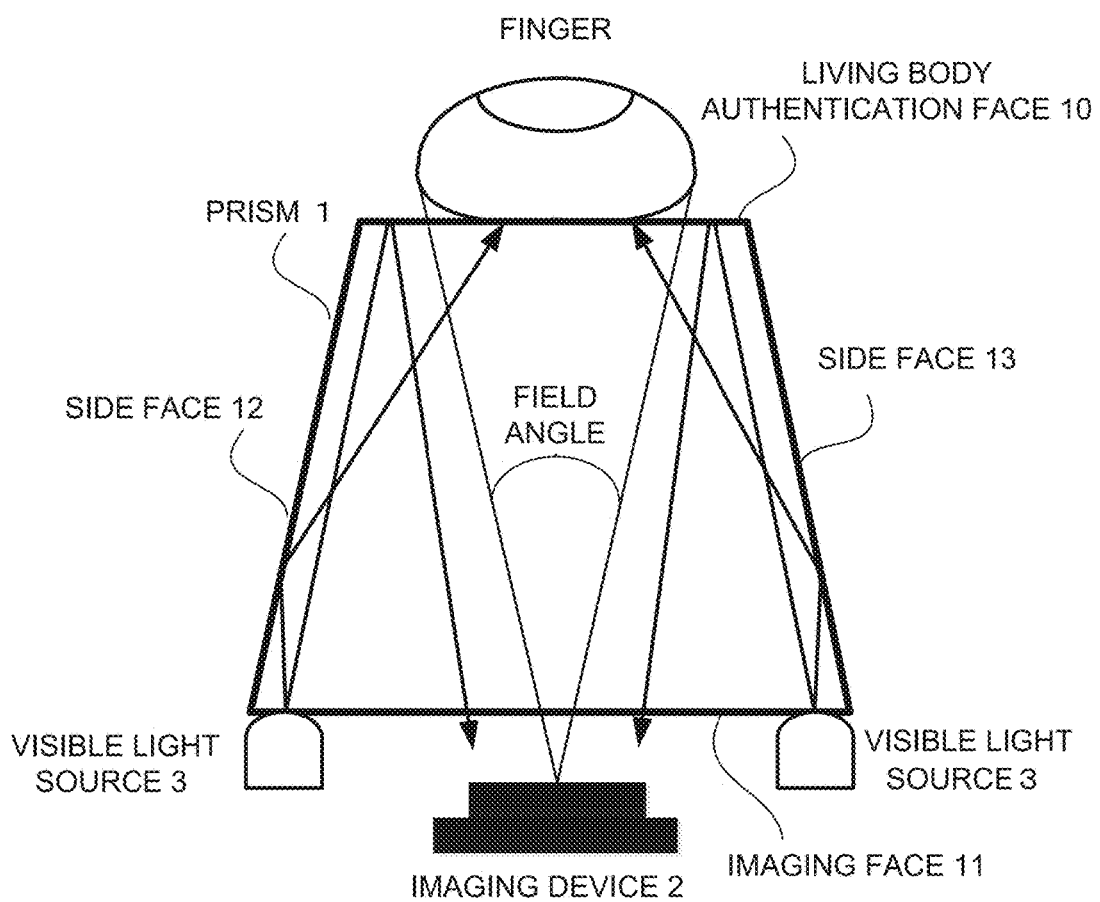
FIG. 3 is a diagram for explaining the prism 1 according to the present invention.

Next, characteristics of the present invention will be described. FIG. 3 is a diagram for explaining the prism 1 according to the present invention. Further, in FIG. 3, 2 designates an imaging device that captures an authentication image of fingerprints of fingers, and 3 designates visible light sources.

The prism 1 is formed in a shape expanded from the living body authentication face 10 toward the imaging face 11. That is, the imaging face 11 is larger than the living body authentication face 10 and the two side faces 12 and 13 of the prism 1 are formed at a slant.

When the visible light sources 3 are disposed below the imaging face 11, part of light radiated from the visible light sources 3 is specularly reflected (totally reflected) by the living body authentication face 10. Further, when viewed from the imaging face 11 side, the visible light sources 3 are reflected on the living body authentication face 10 as point sources of light. Accordingly, when the point sources of the visible light sources 3 reflected on the living body authentication face 10 are captured with an authentication portion (fingerprint matching section including furrows and ridges of the finger) of the finger, its image may be an inappropriate image for authentication in consequence of the point sources of the visible light sources 3.

As a method of solving the above, the living body authentication face 10 and the imaging face 11 are thought to be enlarged sufficiently as compared to a size of the authentication portion of the finger. Using the above method, the prism 1 itself becomes large, and as a result, an increase in the size of the authentication apparatus itself is unavoidable.

To solve the problem, the imaging face 11 is enlarged more than the living body authentication face 10 and a shape of the prism 1 is formed in an expanded shape toward the imaging face 11 from the living body authentication face 10. Further, the visible light sources 3 are disposed in the vicinity of sides coming into contact with the side faces 12 and 13 of the imaging face 11.

According to the configuration described above, when the authentication portion of the finger is put roughly in the center of the living body authentication face 10, the point sources of the visible light sources 3 are not reflected on the living body authentication face 10 against which the authentication portion is put. As a result, the imaging device 2 can capture an image of the authentication portion having no influence on the point sources of the visible light sources 3. Further, an area of the living body authentication face 10 can be reduced, and since the visible light sources 3 are not disposed on the sides of the side faces 12 and 13, the authentication apparatus can be miniaturized.

Further, in the prism 1 according to the present invention, since the side faces 12 and 13 are inclined, light radiated from the visible light sources 3 is reflected by the side faces 12 and 13, and the reflected light illuminates the authentication portion of the finger put against the living body authentication face 10. Therefore, in addition to the above effect, an effect is also obtained that a light amount necessary for capturing increases.

A field angle of the imaging device 2 is a field angle (a field angle somewhat wider than that capable of at least capturing the authentication portion) capable of capturing the authentication portion. In other words, light from the visible light sources 3 that is specularly reflected (totally reflected) by the living body authentication face 10 is not intended to penetrate into the imaging device 2.

In the above-described prism 1, both of the side faces 12 and 13 are inclined. Further, only one side face of the side faces 12 and 13 may be inclined and the visible light source 3 may be disposed only on the inclined side. In this case, the light amount as a whole is reduced, but the same effect as the above-described effect is obtained.

Subsequently, another configuration of the prism 1 according to the present invention will be described.

Figure 4:
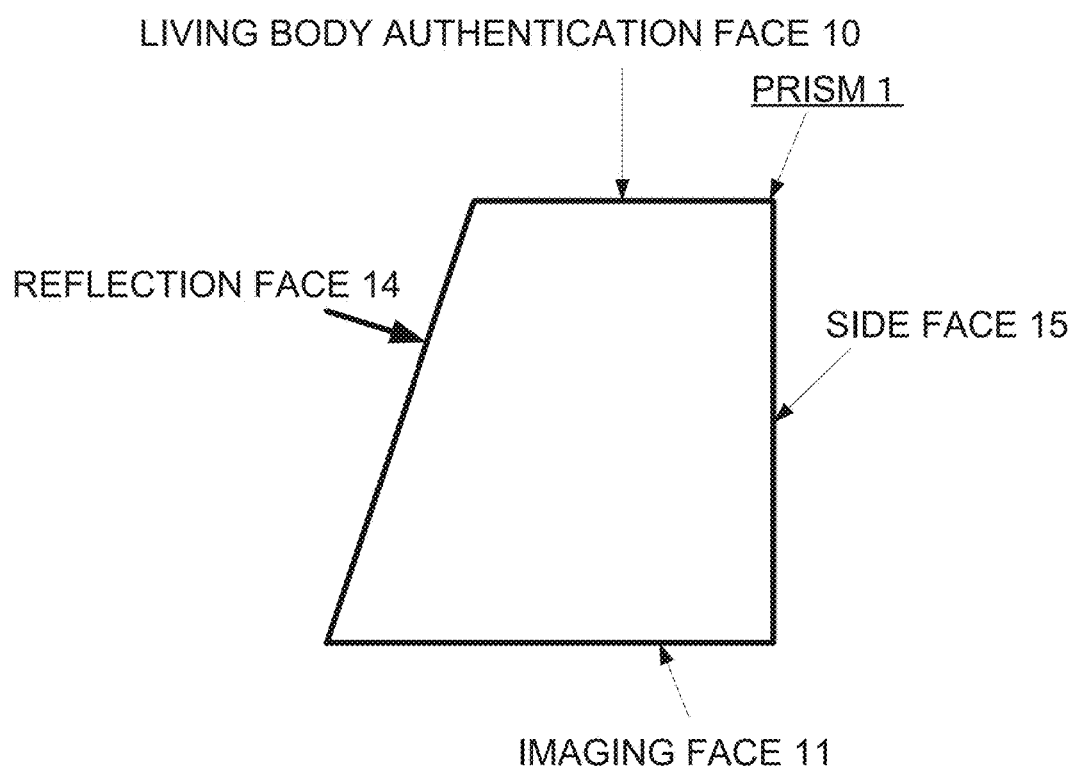
FIG. 4 is a cross-sectional diagram along a B-B' line of the prism 1.

FIG. 4 is a cross-sectional diagram along a B-B' line of the prism 1. In FIG. 4, reference numeral 14 designates a reflection face and 15 designates a side face.

The reflection face 14 is disposed at such an angle that light from the inside of the prism 1 is totally reflected at the living body authentication face 10 in an optical path running from the imaging face 11 and reaching the living body authentication face 10 by way of the reflection face 14. In other words, it is disposed at such an angle that, due to the difference in a refractive index between an air layer and the prism 1 main body, light penetrating into the prism 1 main body from the living body authentication face 10 via the air layer does not reach the reflection face, and at the same time, light reflected off from the living body authentication face 10 is totally reflected toward the imaging face 11.

Next, each optical path will be described with reference to FIGS. 5 to 7. Further, as described above, the present embodiments address a case in which the visible light sources 3 are disposed in the vicinity of the sides coming into contact with the side faces 12 and 13 of the imaging face 11 and the radiated light reflected by furrows and ridges of the finger put against the living body authentication face 10 is captured by an imaging device 2 disposed below the imaging face 11.

Light radiated from the visible light sources 3 is reflected by furrows and ridges of the finger put against the living body authentication face 10.

Figure 5:
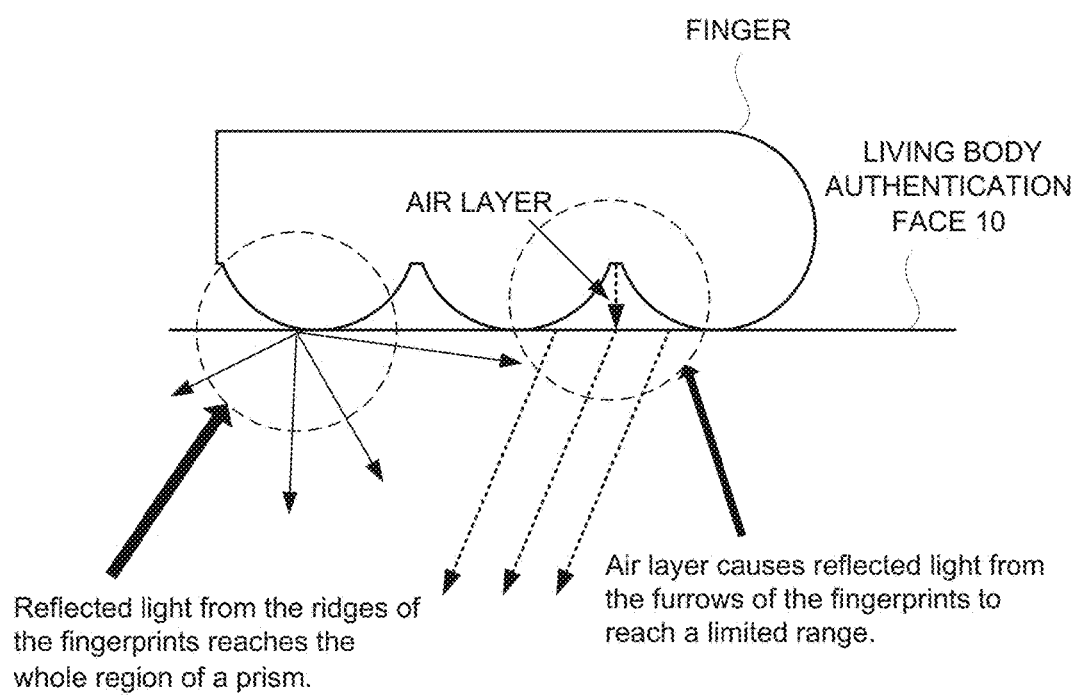
FIG. 5 is a diagram for explaining the prism 1 according to the present invention.
Figure 6:
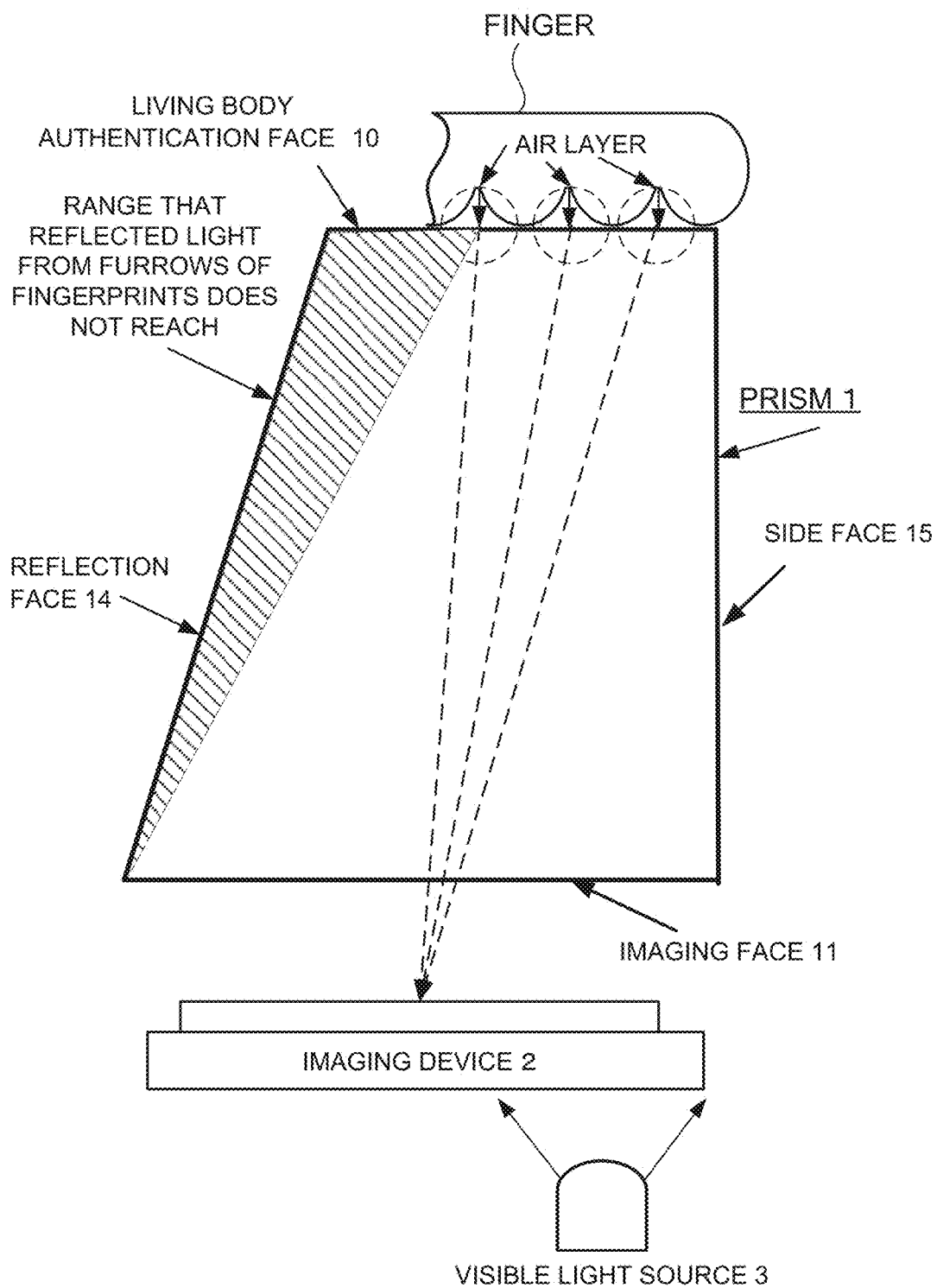
FIG. 6 is a diagram for explaining the prism 1 according to the present invention.

Here, as shown in FIG. 5, the ridges of the finger are in contact with the living body authentication face 10, and therefore, the refractive index of light reflected by the ridges of the finger is approximately the same as that of the prism 1 (glass). Hence, the light reflected by the ridges of the finger may be considered similarly to light reflected at the living body authentication face 10 against which the furrows and ridges of the finger are put, wherein the light is radiated in almost all directions in the inside of the prism 1 and can reach the whole region below the living body authentication face 10.

On the other hand, the furrows of the finger are not in contact with the living body authentication face 10, with an air layer created between the furrows of the finger and the living body authentication face 10. Therefore, reflected light from the furrows of the finger passes through the living body authentication face 10 via the air layer. Since the refractive index, however, is different between the air having a refractive index of 1.0, glass having a refractive index of 1.3 to 1.5, and moisture and skin having a refractive index of 1.3 to 1.4, the reflected light from the furrows of the finger causes a refractive phenomenon different from that by the reflected light from the ridges of the finger, so that the reflected light from the furrows does not radiate in all directions and does not reach a certain range in the inside of the prism 1. The reflected face 14 here is disposed at such an angle that light from the inside of the prism 1 is totally reflected at the living body authentication face 10 in an optical path running from the imaging face 11 and reaching the living body authentication face 10 by way of the reflection face 14. In other words, the reflection face 14 is disposed in a range unreachable by light transmitted through the living body authentication face 10 from the air layer and penetrating into the prism 1, and at the same time, disposed at such an angle that light reflected off from the living body authentication face 10 is totally reflected toward the imaging face 11. Therefore, as shown in FIG. 6, light reflected at the furrows of the finger and transmitted through the living body authentication face 10 via the air layer does not reach the reflection face 14, so that there is no reflected light from the furrows passing from the living body authentication face 10 and reaching the imaging face 11 by way of the reflection face 14, with only reflected light left passing from the living body authentication face 10 and directly reaching the imaging face 11.

Figure 7:
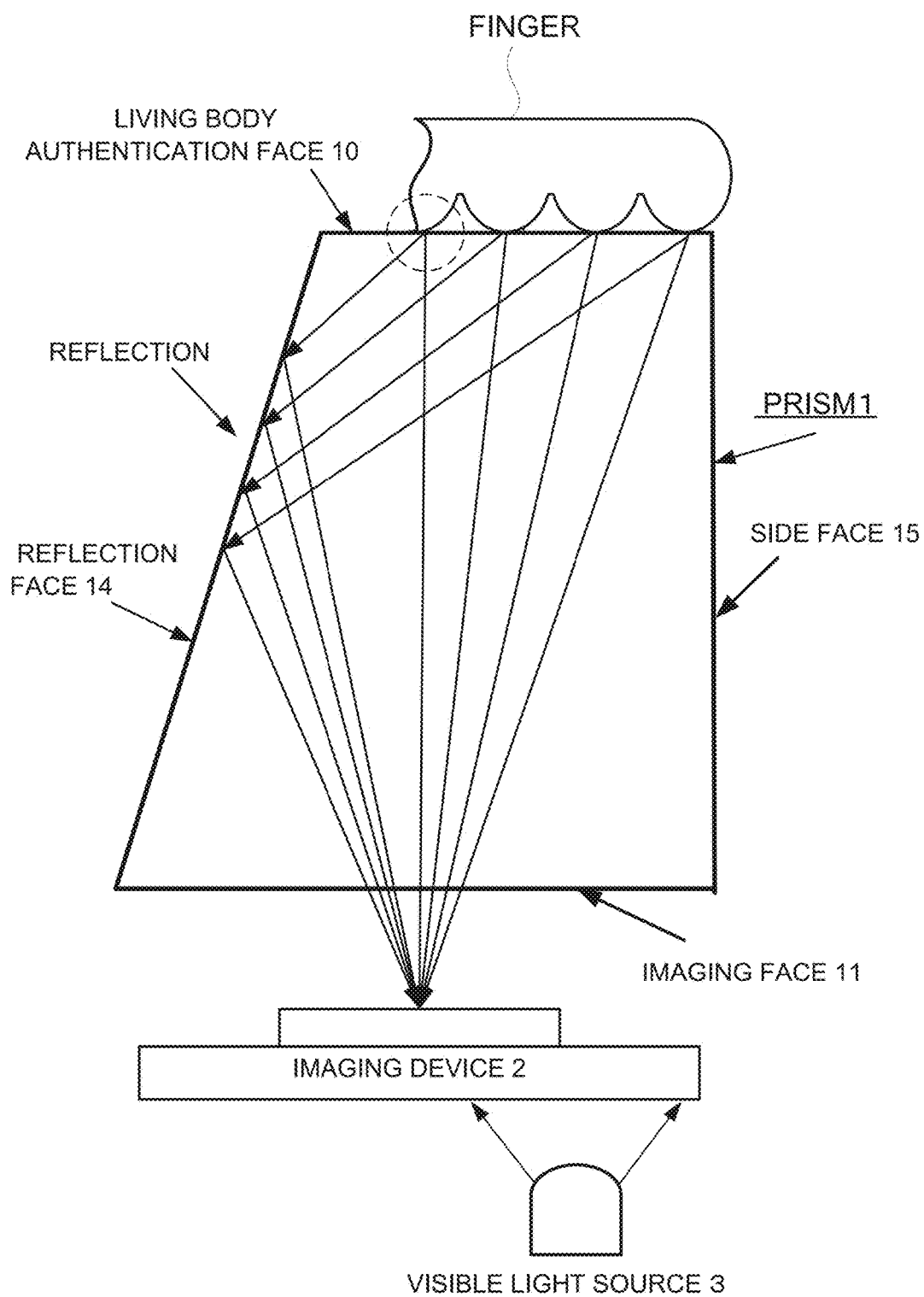
FIG. 7 is a diagram for explaining the prism 1 according to the present invention.

Next, as for the optical paths for the ridges of the finger, light reflected by the ridges of the finger is radiated in almost all directions in the inside of the prism 1 and can reach the whole region below the living body authentication face 10 as described above; as such, the optical paths including those of light directly reaching the imaging face 11 and those of light reflected by the reflection face 14 and reaching the imaging face 11, as shown in FIG. 7.

Figure 8:
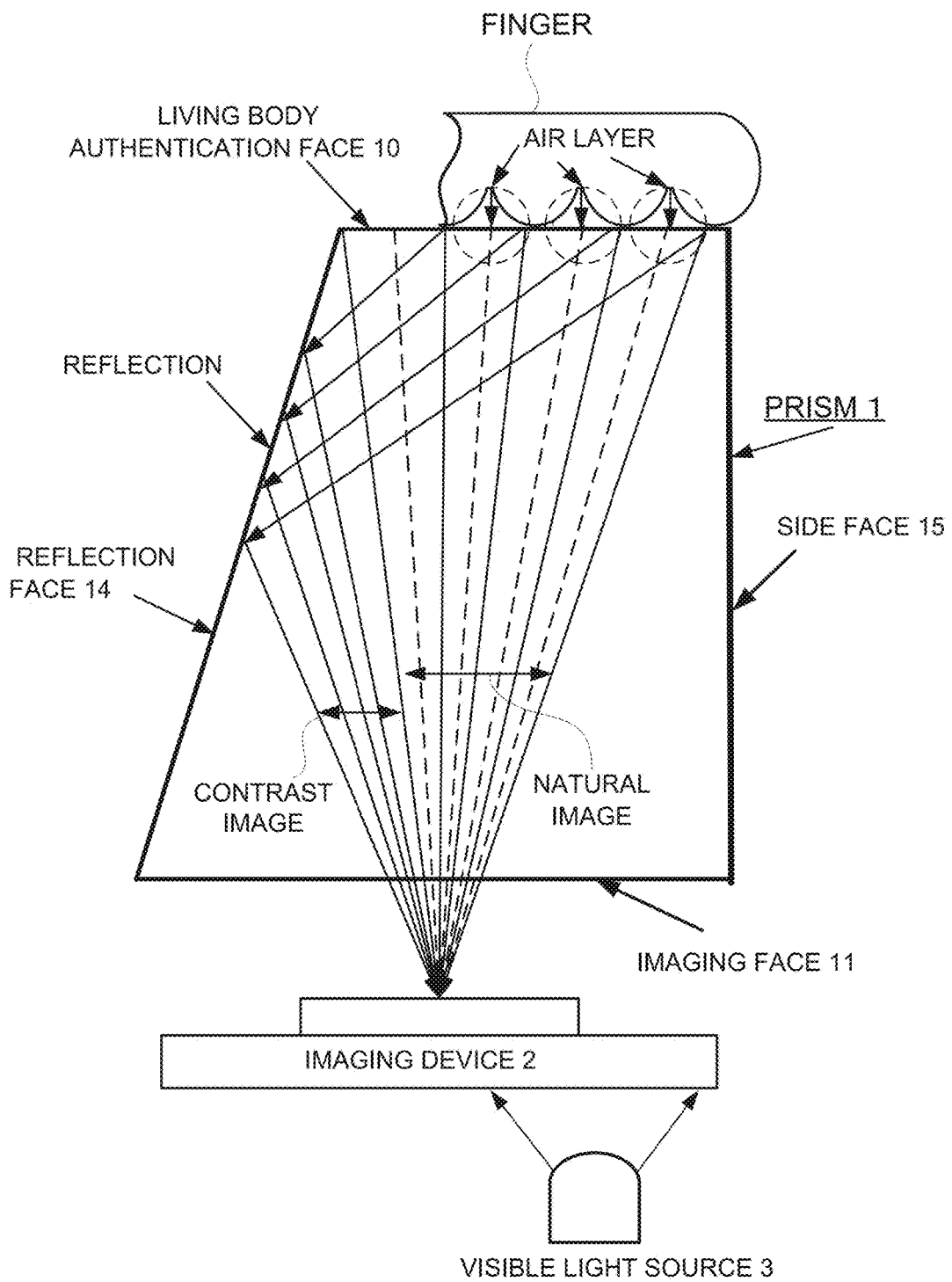
FIG. 8 is a diagram for explaining the prism 1 according to the present invention.

Since the imaging device 2 captures light transmitted through the imaging face 11, as shown in FIG. 8, two kinds of images transmitted through the imaging face 11 are captured. One of them is an image of optical paths of reflected light from the ridges of the finger passing from the living body authentication face 10 and reaching the imaging face 11 by way of the reflection face 14. Since this image is by only reflected light from the ridges of the finger, it is a fingerprint image with high contrast (hereinafter, referred to as a high-contrast image) having dark furrows of the finger and bright ridges of the finger. The other one is an image for optical paths of part of the reflected light reflected by the furrows and ridges of the finger put against the living body authentication face 10 that directly reaches the imaging face 11. Since this image is similar to that of the finger put against the living body authentication face 10 as directly viewed from the imaging face 11, the image captured by the imaging device 2 is a natural image of the finger (hereinafter, referred to as a natural image).

By using the prism 1 as described above in the authentication apparatus, the imaging device 2 can capture a high-contrast image and a natural image by one image capturing, as shown in FIG. 8.

Since it is sufficient for the natural image to allow judgment as to whether the fingerprints are fake or genuine, acquisition of a wide-area image is not necessary. Rather, it is more desirable to analyze an enlarged image in detail. In the capturing of the finger using the prism 1 according to the present embodiment, the optical path for obtaining a natural image is an optical path running from the living body authentication face 10 and directly reaching the imaging face 11, which is the shortest optical path, and therefore, a natural image enlarged enough to detect counterfeits can be obtained.

On the other hand, sine the high-contrast image is used in fingerprint matching, it is more desirable to acquire a fingerprint image in a wider area so that many feature points are present. To acquire a fingerprint image in a wider area, it is necessary to lengthen the optical path from the living body authentication face 10 to the imaging face 11. In the capturing of the finger using the prism 1 according to the present embodiment, the optical path for obtaining a high-contrast image is an optical path running from the living body authentication face 10 to the imaging face 11 by way of the reflection face 14, and therefore, the optical path is long enough to capture a fingerprint image in a wide area such that many feature points are present.

Moreover, the contrast of a high-contrast image may be enhanced more by applying a black coating to the side face 15 or attaching a blackboard to the side face 15.

Further, mirror coating may be applied to the reflection face 14 to enhance reflectance more.

Hereinafter, embodiments will be described in detail.

First Embodiment

A first embodiment will be described.

Figure 9:
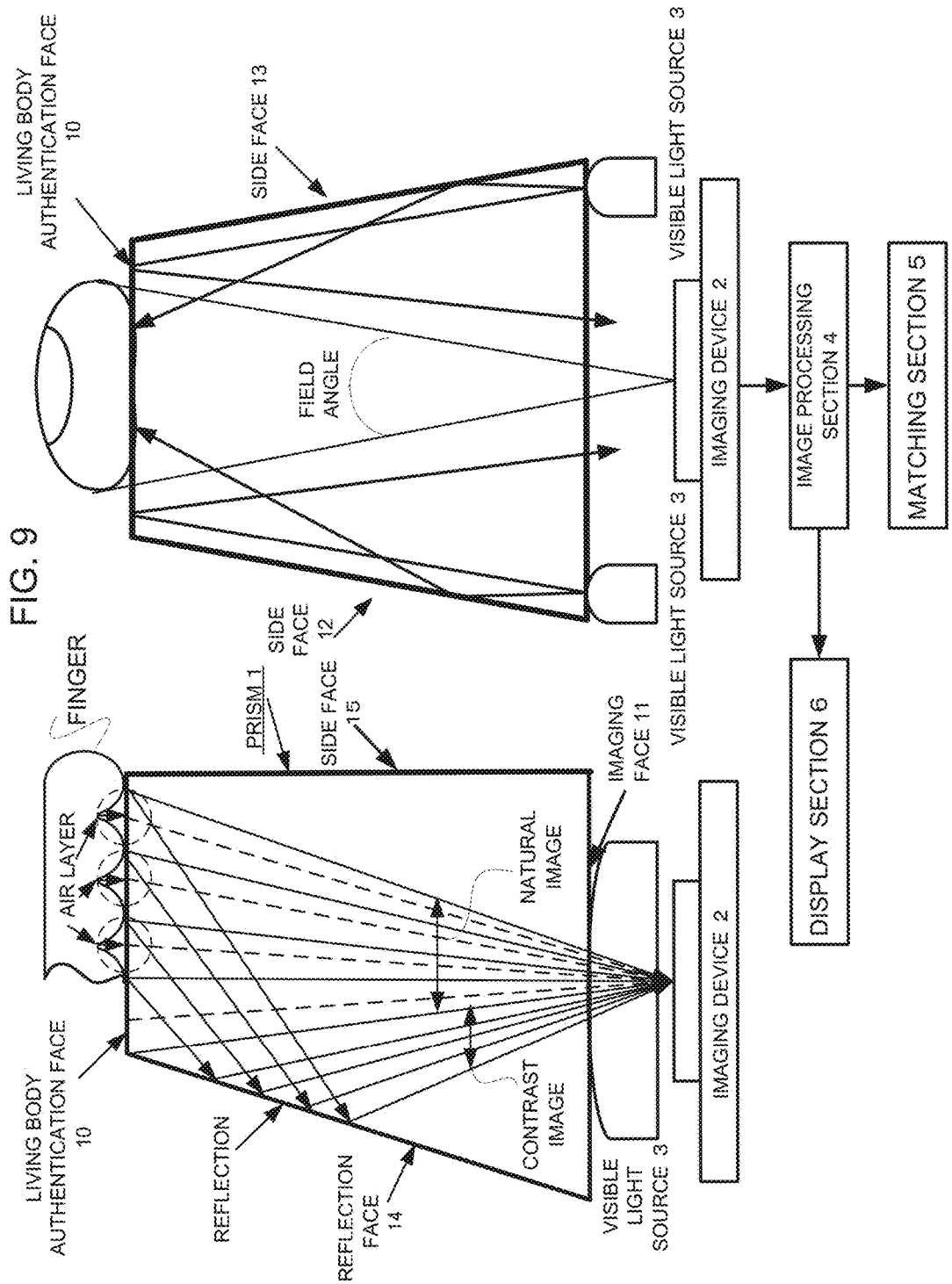
FIG. 9 is a configuration diagram of a fingerprint authentication apparatus in a first embodiment.

FIG. 9 is a configuration diagram of a fingerprint authentication apparatus according to the first embodiment.

In the fingerprint authentication apparatus according to the first embodiment, the prism 1 described above is disposed in a position such that the living body authentication face 10 is disposed above the apparatus to serve as a face against which a fingerprint portion of a finger is put.

The imaging device 2 is disposed below the imaging face 11 of the prism 1. When the authentication portion of the finger is put approximately in the middle of the living body authentication face 10, the field angle of the imaging device 2 is made to be a field angle (a field angle somewhat wider than the field angle capable of at least capturing the authentication portion) capable of capturing the authentication portion. The imaging device 2 converts an input image into digital signals and outputs them, and as image sensor constituted of a CCD (Charge Coupled Device), a CMOS (Complementary MOS), or the like can be used for the imaging device 2.

The visible light sources 3 are disposed below the imaging face 11, and in the vicinity of the sides coming into contact with the side faces 12 and 13. Further, a white lamp bulb, an LED (Light Emitting Diode), or the like is considered as the visible light source 3.

An image processing section 4 converts an image captured by the imaging device 2 into a prespecified image format, and separates the image into a high-contrast image and a natural image, whereupon the high-contrast image is output to a matching section 5 while the natural image is output to a display section 6. In the high-contrast image, trapezoidal distortion occurs in the same manner as in a conventional triangular prism, and therefore correction of the trapezoidal distortion is also performed.

The matching section 5 receives the high-contrast image from the image processing section 4, and performs matching of fingerprints. The fingerprint matching method may be achieved by using any conventional matching method.

The display section 6 receives the natural image from the image processing section 4, and displays the natural image. Thus, criminal acts may be detected, including use of a finger fabricated from resin such as silicone, and identity theft by attaching a semitransparent bumpy film imitating fingerprints to a real fingertip to pretend to be someone else.

Next, operations of the living body authentication apparatus described above will be described.

First, for authentication, a finger is put against the living body authentication face 10 serving as a face for putting fingers in the prism 1.

With the fingerprint portion of the finger put against the living body authentication face 10 of the prism 1, the visible light sources 3 radiate light to the finger for capturing it.

The light radiated from the visible light sources 3 is reflected by the furrows and ridges of the finger in contact with the living body authentication face 10.

Here, since the air has a refractive index of 1.0 while glass has a refractive index of 1.3 to 1.5 and moisture and skin have a refractive index of 1.3 to 1.4, resulting in different refractive indices, reflected light from the furrows of the finger penetrating into the inside of the prism 1 via the air layer cannot reach the reflection face 14, so that only reflected light directly coming from the living body authentication face 10 reaches the imaging face 11.

On the other hand, reflected light from the ridges of the finger radiates in all directions in the inside of the prism 1, and travels toward the reflection face 14 and the imaging face 11. Among these portions of light, some reflected light portions from the ridges traveling toward the reflection face 14 are totally reflected by the reflection face 14 and are directed toward the imaging face 11. Specifically, it is the optical path running from the living body authentication face 10 and reaching the imaging face 11 by way of the reflection face 14.

In the imaging device 2, as one of images to be captured, an image for the optical path running from the living body authentication face 10 and reaching the imaging face 11 by way of the reflection face 14 is captured. The captured image is a high-contrast image in which the ridges of the finger are highlighted.

Further, among the reflected light portions reflected by the furrows and ridges of the finger put against the living body authentication face 10, other portions of the light directly reach the imaging face 11. The reflected light passes through the imaging face 11 and is captured by the imaging device 2. The image by the reflected light is similar to that by directly observing the finger put against the living body authentication face 10 via the imaging face 11, and therefore, the image captured by the imaging device 2 is a natural image in which the furrows and ridges of the finger are captured together.

By light transmitted through the imaging face 11 of the prism 1, through one-time image capturing, the imaging device 2 captures the high-contrast image and the natural image of the fingerprint portion of the finger. At this time, also light (point sources) of the visible light sources 3 that is totally reflected by the living body authentication face 10 is transmitted through the imaging face 11. Due to the field angle of the imaging device 2 and the positions in which the visible light sources 3 are disposed, light from the visible light sources 3 that is specularly reflected by the living body authentication face 10 does not penetrate into the imaging device 2. Therefore, the imaging device 2 can capture an image suitable for authentication and matching having no overexposure part.

Figure 10:
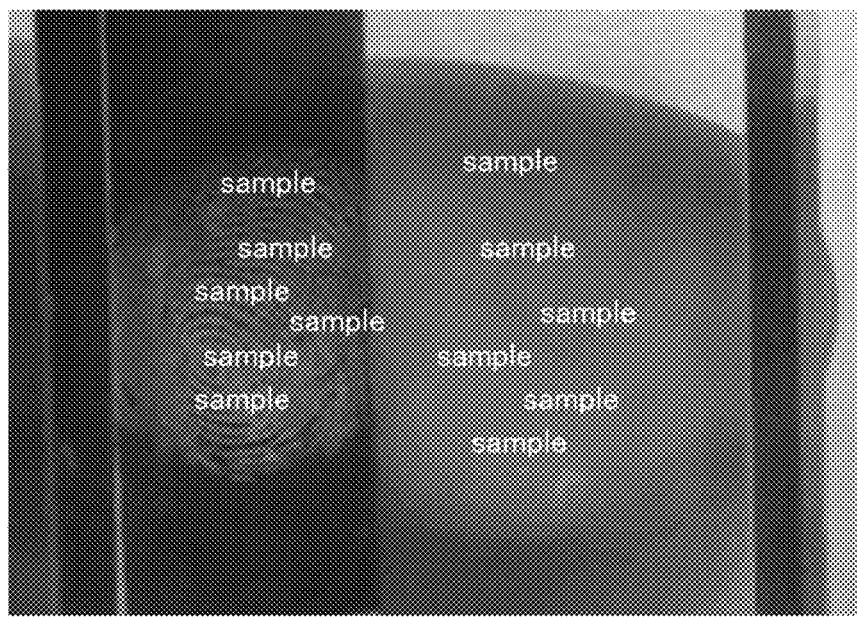
FIG. 10 is one example of an image captured by an authentication apparatus in the first embodiment.

One example of the image captured by the imaging device 2 is shown in FIG. 10. As can be seen from FIG. 10, the point sources of the visible light sources 3 reflected on the living body authentication face 10 are not captured on the captured image. Further, a high-contrast image of the fingerprint portion is captured on the left side of the captured image, and a natural image of the finger including its fingerprint portion is captured on the right side. Of the natural image and the high-contrast image, the natural image is enlarged as compared to the high-contrast image due to the difference in a length of the optical path described above, proving that the natural image enlarged enough to detect a counterfeit can be obtained. On the other hand, it can be seen that the high-contrast image can be obtained as a fingerprint image in a wide area such that many feature points are present.

Processing from emission (radiation) of the visible light sources 3 up to capturing of the imaging device 2 is controlled by an information processing device that operates by programs and a control device (not shown).

The image processing section 4 separates the high-contrast image and natural image obtained by the imaging device 2 from each other, and outputs the high-contrast image to the matching section 5 after correcting trapezoidal distortion, and outputs the natural image to the display section 6.

The matching section 5 applies extraction/matching of the feature quantity to the high-contrast image to achieve fingerprint matching and authentication.

The natural image is displayed on the display section 6 to allow decision by visual observation as to whether a fake fingerprint film, tape, or the like is used during matching.

Thus, the authentication apparatus according to the first embodiment can provide a natural image similar to visual observation for deciding whether a fake fingerprint film, tape, or the like suitable for matching and authentication having no overexposure part is used and an image with high contrast used for matching fingerprints by one imaging device and by one capturing of fingers. Moreover, a natural image enlarged enough to detect a counterfeit may be obtained.

Second Embodiment

A second embodiment will be described.

Figure 11:
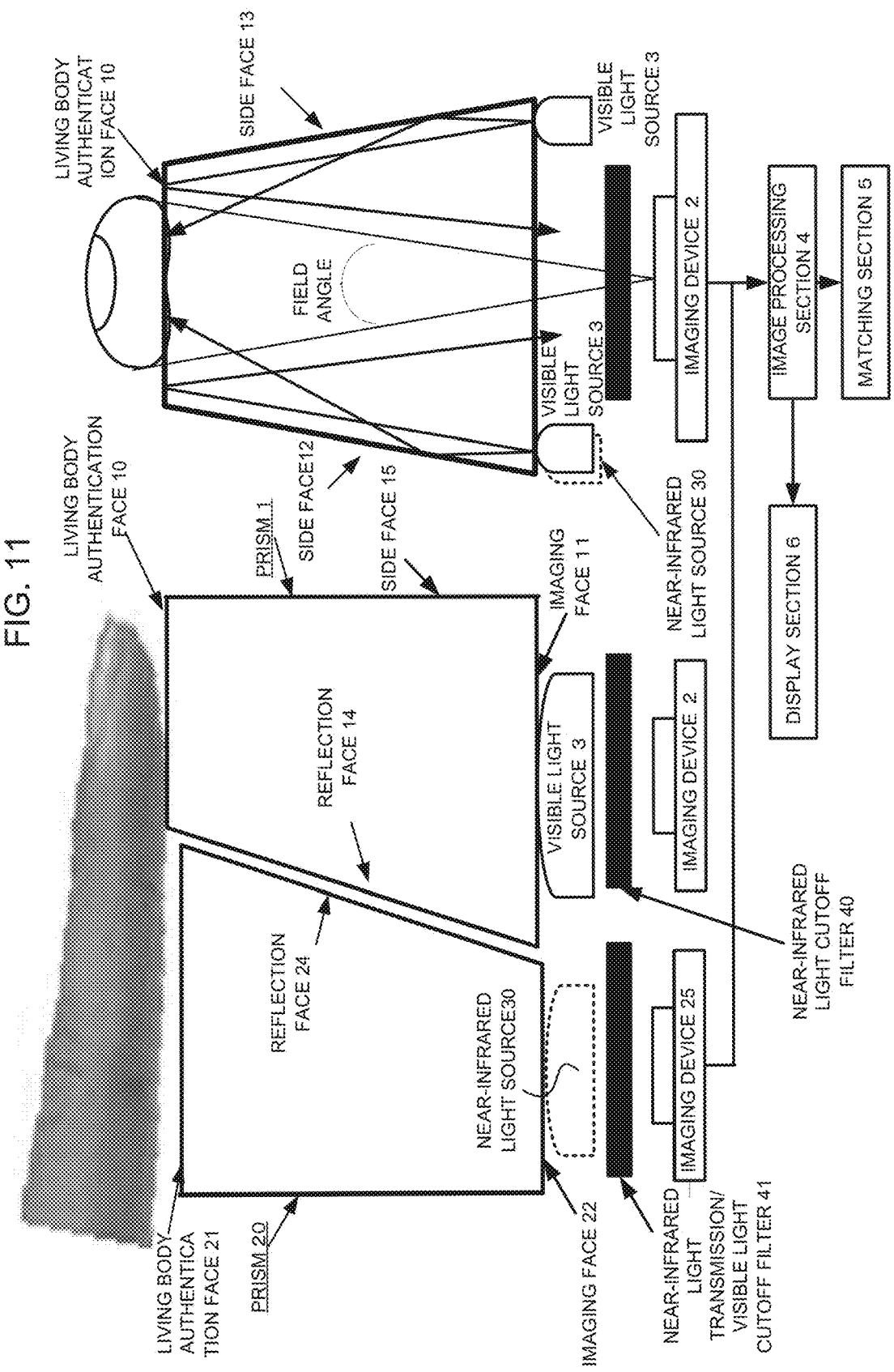
FIG. 11 is a configuration diagram of an authentication apparatus in a second embodiment.

FIG. 11 is a configuration diagram of an authentication apparatus according to the second embodiment.

The second embodiment addresses an example in which, in addition to the configuration of the first embodiment, an infrared light source is disposed to capture a blood vessel pattern of a finger.

According to the second embodiment, a second prism 20 is further used in which the living body authentication face 10 of the prism 1 used in the first embodiment is used as an imaging face 22 and the imaging face 11 of the prism 1 is used as a living body authentication face 21. Further, the prism 1 and the prism 20 are disposed so that the reflection face 14 of the prism 1 and a reflection face 24 of the prism 20 are opposed to each other. Further, the prism 1 and the prism 20 are disposed so that the living body authentication face 21 of the prism 20 becomes lower than the living body authentication face 10 of the prism 1 in the vertical direction. In other words, a fingerprint portion of a finger is brought into contact with the living body authentication face 10 of the prism 1, and further the prism 1 and the prism 20 are disposed in a height and a position such that a finger portion in which a blood vessel pattern of the finger is captured is not brought into contact with the living body authentication face 21 of the prism 20. The reason is that the finger portion in which the blood vessel pattern of the finger is captured is brought into contact with the living body authentication face 21 of the prism 20, and thereby the fact is avoided that the finger portion is pressed and a preferable blood vessel pattern cannot be captured.

Further, as shown in FIG. 11, a near-infrared light source 30 is disposed in the vicinity of a side coming into contact with a side face of the imaging face 22 of the prism 20. In the near-infrared light source 30, near-infrared light having a wavelength ranging from 700 to 1000 nm is preferable in which oxyhemoglobin in blood is favorably absorbed and sensitivity to biological pigments is low.

Further, an imaging device 25 having sensitivity for near-infrared light is disposed below the imaging face 22 of the prism 20. Further, a near-infrared light transmission/visible light cutoff filter 41 for transmitting near-infrared light and cutting off visible light is provided between the imaging device 25 and the imaging face 22. Thus, visible light is cut off and only infrared light penetrates into the imaging device 25.

Further, a near-infrared light cutoff filter 40 for transmitting visible light and cutting off near-infrared light is provided between the imaging device 2 and the imaging face 11. Thus, only visible light penetrates into the imaging device 2.

By the above-described configuration, at the same time, the visible light sources 3 that are visible light sources radiate light, and the near-infrared light source 30 that is a near-infrared light source radiates light. The imaging device 2 captures a natural image and a high-contrast image, and the imaging device 25 captures a blood vessel pattern of a finger.

According to the second embodiment, in addition to the effects in the first embodiment, variation of an image due to blood-flow-induced pulsation and subcutaneous tissue may be observed for use in living body identification to achieve living body identification with higher precision. In particular, a finger portion in which a blood vessel pattern of a finger is captured is not pressed by the living body authentication face 21 of the prism 20, and therefore a preferable blood vessel pattern can be captured.

Third Embodiment

A third embodiment will be described.

Figure 12:
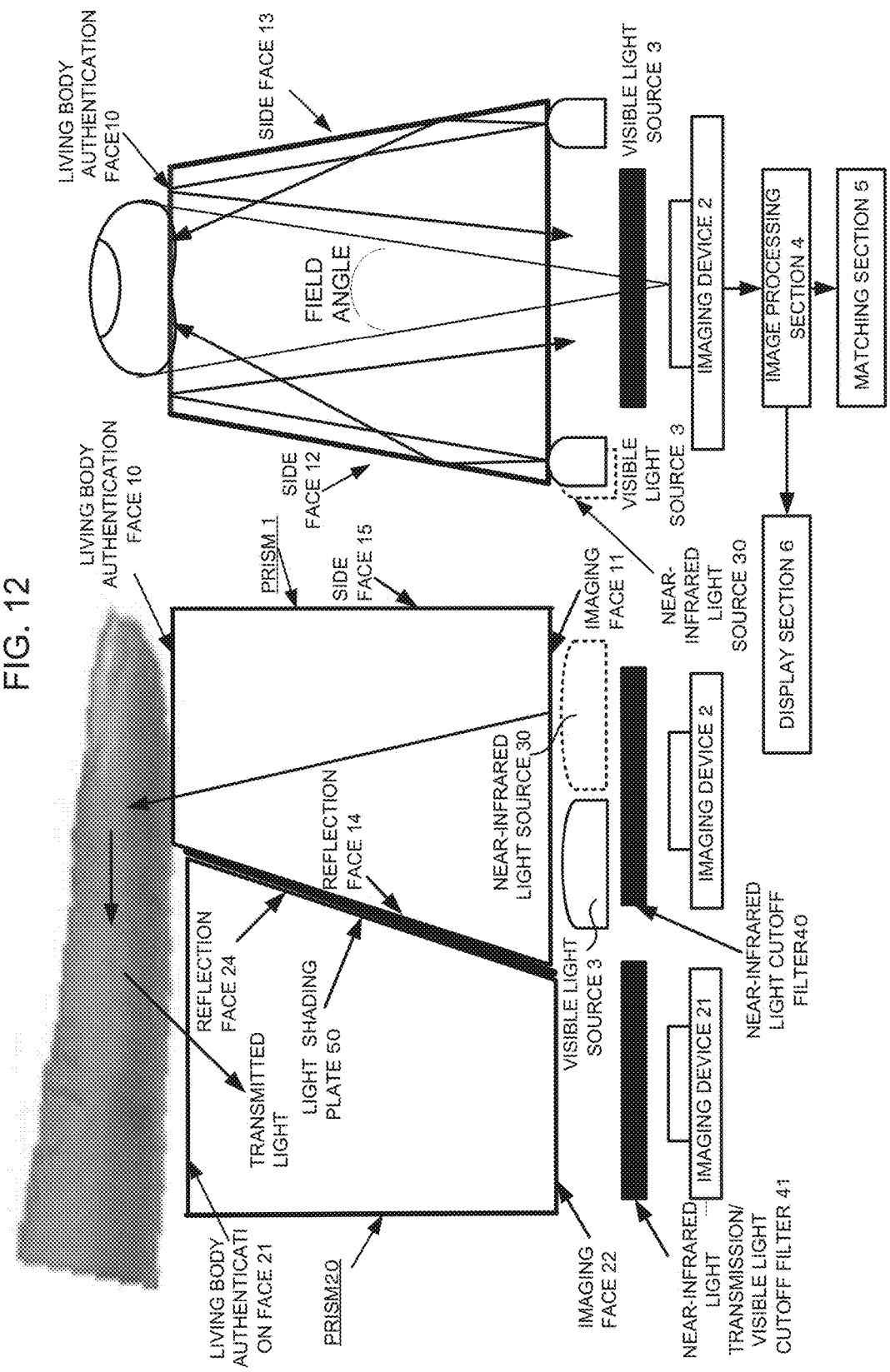
FIG. 12 is a configuration diagram of an authentication apparatus in a third embodiment.

FIG. 12 is a configuration diagram of an authentication apparatus according to the third embodiment.

The third embodiment has a configuration in which, in addition to the prism configuration of the second embodiment, the near-infrared light source 30 is disposed below the imaging face 11 side of the prism 1. Further, the third embodiment addresses an example in which near-infrared light radiated from the near-infrared light source 30 captures light that is scattered and transmitted inside a finger and captures a blood vessel pattern of the finger.

A configuration of the third embodiment is different from that of the second embodiment in that the near-infrared light source 30 that is disposed below the imaging face 22 of the prism 20 is disposed below the imaging face 11 side of the prism 1. Further, near-infrared light radiated from the near-infrared light source 30 is prevented from being transmitted through the prism 1 and penetrating into the prism 20, and therefore a light shading plate 50 that shades near-infrared light is provided between the reflection face 14 of the prism 1 and the reflection face 24 of the prism 20. Light shielding coating that shades near-infrared light may be applied to the outside of the reflection face 14 of the prism 1 and the reflection face 24 of the prism 20.

According to the configuration described above, the visible light sources 3 and the near-infrared light source 30 may be simultaneously activated to radiate light, whereby capturing of a natural image and a high-contrast image by the imaging device 2 and capturing of a blood vessel pattern of a finger through transmitted light by the imaging device 25 may be simultaneously achieved, so that a natural image and a high-contrast image, as well as an image of a blood vessel pattern of a finger may be simultaneously obtained through one-time image capturing.

According to the third embodiment, since capturing of the blood vessel pattern is achieved through transmitted light, a clearer image of the blood vessel pattern may be obtained as compared to reflected light.

Fourth Embodiment

A fourth embodiment will be described.

Figure 13:
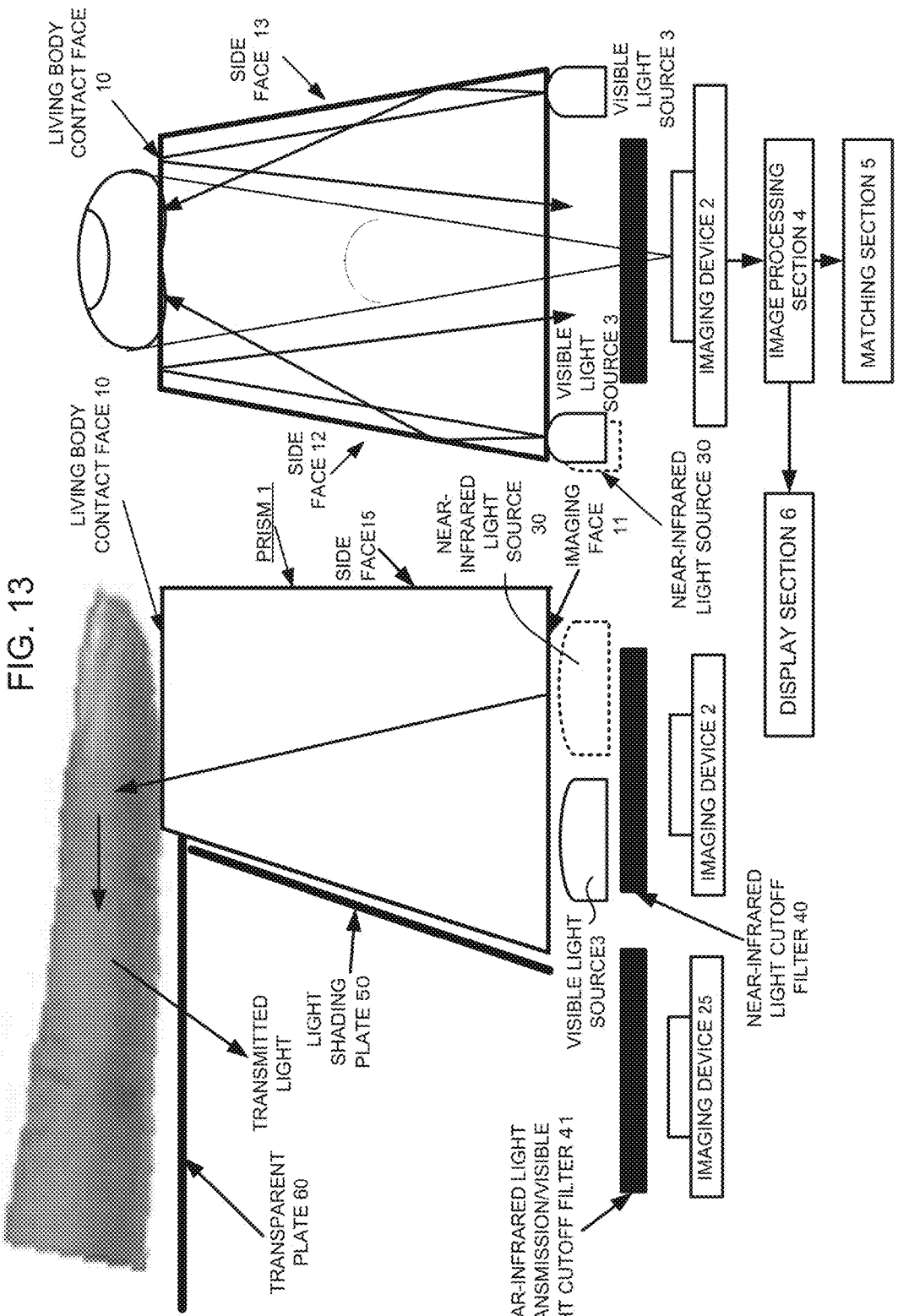
FIG. 13 is a configuration diagram of an authentication apparatus in a fourth embodiment.

FIG. 13 is a configuration diagram of an authentication apparatus according to the fourth embodiment.

A configuration of the fourth embodiment has an aspect in which the prism 20 is removed from a configuration of the third embodiment, and the other configuration of the fourth embodiment is the same as that of the third embodiment.

In the fourth embodiment, in order that dust may be prevented from entering the apparatus in place of using the prism 20, a transparent plate 60 is provided at the same height as that of the living body authentication face 21 of the prism 20.

Thus, the same effects as those of the third embodiment can be obtained.

Figure 14:
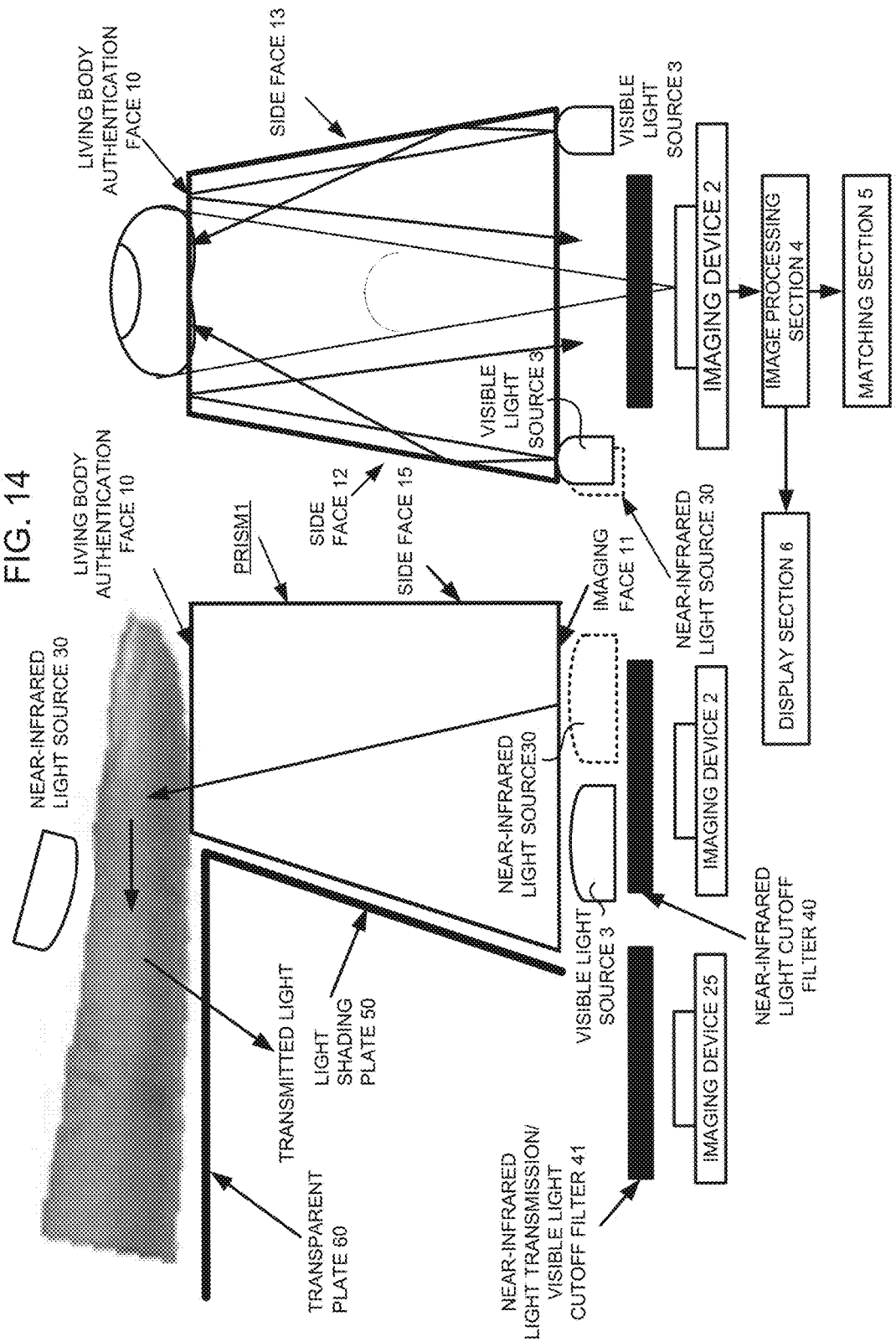
FIG. 14 is a configuration diagram of an authentication apparatus of a modification example of the fourth embodiment.
Figure 15:
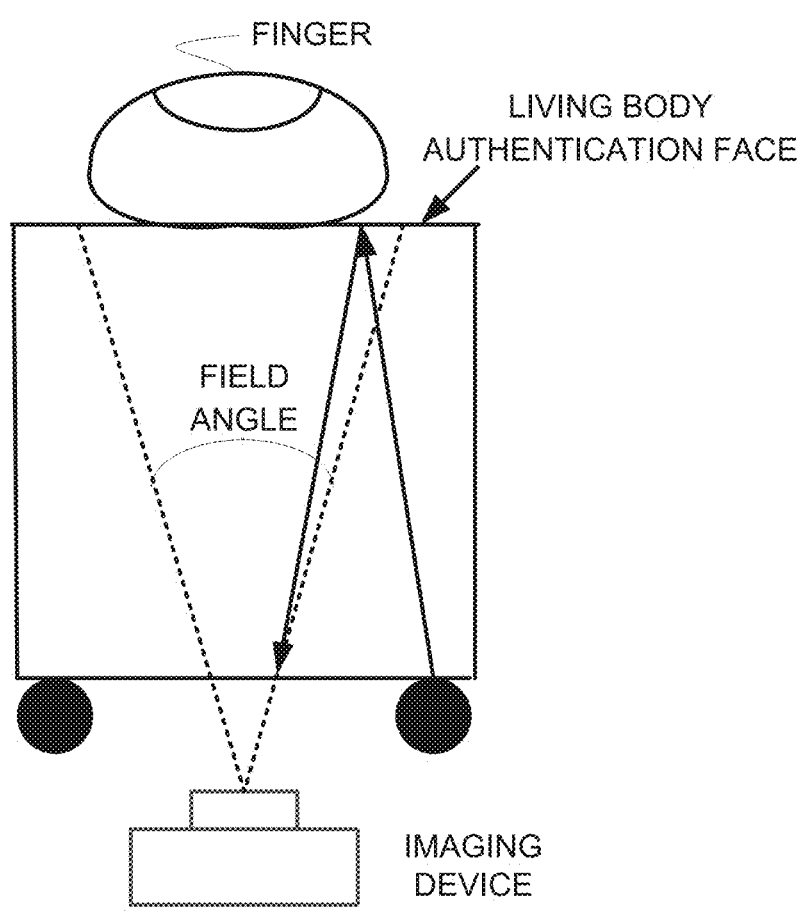
FIG. 15 is a diagram for explaining a related authentication apparatus.

In the third or fourth embodiment, the near-infrared light source 30 is further disposed over a finger as shown in FIG. 14, and thereby a clearer image of a blood vessel pattern can be captured.

As is obvious from the preceding description, while several parts may be configured in hardware, they also may be implemented by a computer program. In this case, a processor that is operated by programs stored in a program memory implements functions and/or operations similar to those in the embodiments described above. Moreover, only part of functions of the embodiments described above may be implemented by a computer program.

Further, part of all of the preceding embodiments may be described as in the following appendices, although not limited thereto.

(Supplementary Note 1) An authentication apparatus comprising a prism member, an imaging unit, and a visible light source configured to radiate visible light to a living body, wherein:

said prism member has a substantially trapezoidal shape with at least one side face thereof formed in an expanded shape from a living body authentication face against which an authentication portion of said living body is put, toward an imaging face that is parallel to said living body authentication face, said visible light source is disposed below said imaging face and near a side of an expanded side of said imaging face, and said imaging unit is disposed below said imaging face.

(Supplementary Note 2) The authentication apparatus according to supplementary note 1, wherein:

said prism member is formed in an expanded shape in two side faces from said living body authentication face against which said authentication portion of said living body is put, toward said imaging face that is parallel to said living body authentication face.

(Supplementary Note 3) The authentication apparatus according to supplementary note 1 or 2, wherein:

said prism member comprises a reflection face configured to be a side face that is not opposed to a side face of said expanded side and totally reflects light reflected by said living body authentication face toward said imaging face, and captures living-body reflected light in which light radiated from said visible light source is reflected by an authentication portion of said living body in contact with said living body authentication face and reflection face reflected light in which said living-body reflected light is reflected by said reflection face.

(Supplementary Note 4) The authentication apparatus according to supplementary note 3, wherein:

an image obtained by capturing said living-body reflected light is a natural image for detecting a counterfeit, and an image obtained by capturing said reflection face reflected light is a contrast image for authentication of said living body.

(Supplementary Note 5) The authentication apparatus according to supplementary note 3 or 4, wherein:

said prism member comprises an opposite face configured to be generally perpendicular contact with said living body authentication face and said imaging face, and to be formed at a position opposite to said reflection face, and at least part of said opposite face is coated with black or attached with a blackboard.

(Supplementary Note 6) The authentication apparatus according to any one of supplementary notes 3 through 5, wherein:

mirror coating is applied to said reflection face.

(Supplementary Note 7) The authentication apparatus according to any one of supplementary notes 1 through 6, comprising:

a second prism member configured to use said living body authentication face of said prism member as an imaging face, and use said imaging face of said prism member as a living body authentication face;

an infrared light source; and a second imaging unit, wherein:

said prism member and said second prism member are disposed so that said reflection face of said prism member and a reflection face of said second prism member are opposed to each other, said infrared light source and said second imaging unit are disposed below and imaging face of said second prism member, said infrared light source radiates infrared light to a second authentication portion of said living body, and said second imaging unit captures reflected light in which said radiated infrared light is reflected by said second authentication portion of said living body.

(Supplementary Note 8) The authentication apparatus according to any one of supplementary notes 1 through 6, comprising:

a second prism member configured to use said living body authentication face of said prism member as an imaging face, and use said imaging face of said prism member as a living body authentication face;

an infrared light source; and a second imaging unit, wherein:

said prism member and said second prism member are disposed so that said reflection face of said prism member and a reflection face of said second prism member are opposed to each other, said infrared light source is disposed below said imaging face of said prism member, said second imaging unit is disposed below said imaging face of said second prism member, said infrared light source radiates infrared light to a first authentication portion of said living body, and said second imaging unit captures infrared light that penetrates into said first authentication portion of said living body and is transmitted through a second authentication portion of said living body.

(Supplementary Note 9) The authentication apparatus according to supplementary note 7 or 8, wherein:

a light shading member is provided between said reflection face of said prism member and that of said second prism member.

(Supplementary Note 10) The authentication apparatus according to any one of supplementary notes 7 through 9, wherein:

said prism member and said second prism member are disposed so that said living body authentication face of said second prism member becomes lower than that of said prism member.

(Supplementary Note 11) The authentication apparatus according to any one of supplementary notes 1 through 6, comprising:

an infrared light source configured to be disposed below said prism member; and a second imaging unit configured to be disposed below said second authentication portion of said living body, wherein:

said infrared light source radiates infrared light to said first authentication portion of said living body, and said second imaging unit captures infrared light that penetrates into said first authentication portion of said living body and is transmitted through said second authentication portion of said living body.

(Supplementary Note 12) The authentication apparatus according to supplementary note 11, wherein:

a transmission member for preventing powder dust into an inside of said authentication apparatus is provided by forming a step so as to become lower than said living body authentication face of said prism member.

(Supplementary Note 13) The authentication apparatus according to supplementary note 11 or 12, wherein:

a light shading member is provided on the side of said reflection face of said prism member.

(Supplementary Note 14) The authentication apparatus according to any one of supplementary notes 1 through 13, wherein:

said living body is a human finger.

(Supplementary Note 15) A prism member for authentication of a living body, comprising:

a living body authentication face configured to put an authentication portion of said living body; and an imaging face configured to be parallel to said living body authentication face, wherein:

said prism member has a substantially trapezoidal shape with at least one side face thereof formed in an expanded shape from said living body authentication face toward said imaging face.

(Supplementary Note 16) The prism member according to supplementary note 15, wherein:

said prism member is formed in an expanded shape in two side faces from said living body authentication face against which said authentication portion of said living body is put, toward said imaging face that is parallel to said living body authentication face.

(Supplementary Note 17) The prism member according to supplementary note 15 or 16, wherein:

said prism member comprises a reflection face configured to be a side face that is not opposed to a side face of said expanded side and totally reflects light reflected by said living body authentication face toward said imaging face, and captures living-body reflected light in which light radiated from said visible light source is reflected by an authentication portion of said living body in contact with said living body authentication face and reflection face reflected light in which said living-body reflected light is reflected by said reflection face.

(Supplementary Note 18) The prism member according to supplementary note 17, wherein:

said prism member comprises an opposite face configured to be in generally perpendicular contact with said living body authentication face and said imaging face, and to be formed at a position opposite to said reflection face, and at least part of said opposite face is coated with black or attached with a blackboard.

(Supplementary Note 19) The prism member according to any one of supplementary notes 15 through 18, wherein:

mirror coating is applied to said reflection face.

(Supplementary Note 20) A capturing method for use in an authentication apparatus including a prism member that has a substantially trapezoidal shape with at least one side face thereof formed in an expanded shape from a living body authentication face against which an authentication portion of a living body is put, toward an imaging face that is parallel to said living body authentication face, said method comprising:

radiating visible light to a living body via said prism member from a lower part of said imaging face and the vicinity of a side on the expanded side of said imaging face; and capturing said living body by an imaging device from said imaging face side.

(Supplementary Note 21) A program for use in an authentication apparatus including a prism member that has a substantially trapezoidal shape with at least one side face thereof formed in an expanded shape from a living body authentication face against which an authentication portion of a living body is put, toward an imaging face that is parallel to said living body authentication face, said program causing an information processing device to perform a capturing procedure comprising:

radiating light from a visible light source that is disposed below said imaging face and in the vicinity of a side on the expanded side of said imaging face; and capturing said living body via said imaging face by an imaging unit that is disposed below said imaging face.

While the present invention has been described with reference to the preferred embodiments, it is not necessarily limited to the embodiments described above, and may be practiced with several modifications within a scope of the technical idea thereof.

The present application claims priority based on Japanese Patent Application No. 2013-272614 filed on Dec. 27, 2013, disclosure of which is incorporated herein in its

REFERENCE SIGNS LIST

1 Prism
2 Imaging device
3 Visible light source
4 Image processing section
5 Matching section
6 Display section
10 Living body authentication face
11 Imaging face
12 Reflection face
13 Face
20 Prism
25 Imaging device
30 Near-infrared light source
40 Near-infrared light cutoff filter
41 Near-infrared light transmission/visible light cutoff filter
50 Light shading plate
60 Transparent plate

The invention claimed is:

1. An authentication apparatus comprising a first prism member, an imaging unit, and a visible light source that radiates visible light to a living body, wherein:

said first prism member has a substantially trapezoidal shape with at least one side face thereof formed in an expanded shape from a living body authentication face against which an authentication portion of said living body is put, toward an imaging face that is parallel to said living body authentication face, said visible light source is disposed below said imaging face and near a side of an expanded side of said imaging face, and said imaging unit is disposed below said imaging face, said authentication apparatus further comprising:

a second prism member, wherein said living body authentication face of said first prism is an imaging face of said second prism member, and said imaging face of said first prism member is a living body authentication face of said second prism member;

an infrared light source; and a second imaging unit, wherein:

said first prism member and said second prism member are disposed so that a reflection face of said first prism member and a reflection face of said second prism member are opposed to each other, said infrared light source and said second imaging unit are disposed below said imaging face of said second prism member, said infrared light source radiates infrared light to an authentication portion of said living body, and said second imaging unit captures reflected light in which said radiated infrared light is reflected by said authentication portion of said living body, wherein a light shading member is provided between said reflection face of said first prism member and said reflection face of said second prism member.

2. The authentication apparatus according to claim 1, wherein:
said first prism member and said second prism member are disposed so that said living body authentication face of said second prism member is lower than said living body authentication face of said first prism member.

3. The authentication apparatus according to claim 1, wherein:
said living body is a human finger.

4. An authentication method by an authentication apparatus, the authentication apparatus comprising a first prism member, an imaging unit, and a visible light source that radiates visible light to a living body, wherein:
said first prism member has a substantially trapezoidal shape with at least one side face thereof formed in an expanded shape from a living body authentication face against which an authentication portion of said living body is put, toward an imaging face that is parallel to said living body authentication face,
the authentication method comprising:
disposing said visible light source below said imaging face and near a side of an expanded side of said imaging face, and
disposing said imaging unit below said imaging face,
the authentication apparatus further comprising:
a second prism member configured, wherein said living body authentication face of said first prism member is an imaging face of the second prism member, and said imaging face of said first prism member is a living body authentication face of said second prism member;
an infrared light source; and
a second imaging unit, wherein
said first prism member and said second prism member are disposed so that a reflection face of said first prism member and a reflection face of said second prism member are opposed to each other,
said second imaging unit is disposed below said imaging face of said second prism member, and
a light shading member is provided between said reflection face of said first prism member and said reflection face of said second prism member,
the authentication method further comprising:
radiating, with said infrared light source, infrared light to a authentication portion of said living body, and
capturing reflected light, by said second imaging unit, in which said radiated infrared light is reflected by said authentication portion of said living body.

5. The authentication method according to claim 4, further comprising:
disposing said first prism member and said second prism member so that said living body authentication face of said second prism member is lower than said living body authentication face of said prism member.

6. The authentication method according to claim 4, wherein:
said living body is a human finger.

* * * * *